United States Patent [19]

Huss, Jr. et al.

[11] Patent Number: 5,221,777

[45] Date of Patent: Jun. 22, 1993

[54] ISOPARAFFIN:OLEFIN ALKYLATION PROCESS EMPLOYING LEWIS-ACID PROMOTED PILLARED LAYERED SILICATE

[75] Inventors: Albin Huss, Jr., Chadds Ford, Pa.; Ivy D. Johnson, Medford, N.J.

[73] Assignee: Mobil Oil Corporation, Fairfax, Va.

[21] Appl. No.: 713,240

[22] Filed: Jun. 7, 1991

[51] Int. Cl.$^5$ .............................................. C07C 2/60
[52] U.S. Cl. ................................. 585/726; 585/722; 585/727; 585/730
[58] Field of Search ............... 585/723, 726, 727, 730, 585/722

[56] References Cited

U.S. PATENT DOCUMENTS

| | | |
|---|---|---|
| 2,380,234 | 7/1945 | Hall . |
| 2,615,908 | 10/1952 | McCaulay . |
| 3,531,546 | 9/1970 | Hervert . |
| 3,780,130 | 12/1973 | Miller . |
| 3,795,712 | 3/1974 | Torck et al. . |
| 3,856,764 | 12/1974 | Throckmorton et al. . |
| 3,862,258 | 1/1975 | Huang et al. . |
| 4,646,488 | 3/1987 | Burns . |
| 4,783,567 | 11/1988 | Kocal . |
| 4,918,255 | 4/1990 | Chou et al. . |
| 4,935,577 | 6/1990 | Huss, Jr. et al. . |
| 4,938,935 | 7/1990 | Audeh et al. . |
| 4,938,936 | 7/1990 | Yan . |
| 4,985,220 | 1/1991 | Audeh et al. . |
| 4,992,616 | 2/1991 | Chou et al. . |
| 5,008,481 | 4/1991 | Johnson et al. .......... 585/418 |
| 5,012,033 | 4/1991 | Child et al. .......... 585/726 |
| 5,063,039 | 11/1991 | Valyocsik .......... 423/329 |

OTHER PUBLICATIONS

"Alkylation of Isobutane with C$_4$ Olefins", 27 *Ind. Eng. Chem. Res.*, 381–397, (1988).
"*Handbook of Petroleum Refining Processes*", 23–28 (R. A. Meyers, ed., 1986).
"Modern Alkylation" by Lyle F. Albright, *Oil and Gas Journal*, Nov. 12 & 26, 1990.

*Primary Examiner*—Asok Pal
*Attorney, Agent, or Firm*—Alexander J. McKillop; Dennis P. Santini; Robert B. Furr, Jr.

[57] ABSTRACT

A process is provided for alkylating an isoparaffin with an olefin comprising effecting reaction of isoparaffin and olefin in the presence of an alkylation catalyst complex comprising a Lewis acid and a solid component, said solid component comprising a layered silicate and pillars of an oxide of at least one element selected from Groups IB, IIB, IIIA, IIIB, IVA, IVB, VA, VB, VIA, VIIA and VIIIA of the Periodic Table of the Elements separating the layers of the silicate.

13 Claims, No Drawings

ISOPARAFFIN:OLEFIN ALKYLATION PROCESS EMPLOYING LEWIS-ACID PROMOTED PILLARED LAYERED SILICATE

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due to its high octane rating.

Industrial alkylation processes have historically used Bronsted acid catalysts such as hydrofluoric or sulfuric acid under relatively low temperature conditions. Acid strength is preferably maintained at 88 to 94 weight percent by the continuous addition of fresh acid and the continuous withdrawal of spent acid.

Bronsted acid catalyzed isoparaffin:olefin alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 *Handbook of Petroleum Refining Processes* 23-28 (R. A. Meyers, ed., 1986). For a discussion of the safety and environmental concerns associated with liquid Bronsted acid alkylation, see U.S. Pat. Nos. 4,938,935 and 4,985,220 to Audeh and Greco, as well as U.S. Pat. No. 4,938,936 to Yan, which teach methods for containing and/or neutralizing HF acid clouds following accidental releases.

Various hydrofluoric acid catalyst complexes have, in the past, been disclosed as useful for various purposes. However, the prior art has not contemplated the novel catalyst complex and alkylation process of the present invention which improves safety and avoids the environmental hazards associated with HF alkylation processes.

U.S. Pat. No. 2,615,908 to McCaulay teaches thioether-HF-copper complex compounds and a method for preparing the same. Potential uses for the thioether-HF-copper complex compounds are listed from column 6, line 55 through column 8 at line 3. The method is said to be useful for purifying HF-containing vent gases from an industrial HF alkylation plant. See column 7, lines 10-24.

U.S. Pat. No. 3,531,546 to Hervert discloses a HF-$CO_2$ catalyst complex which is said to be useful for alkylation as well as olefin isomerization.

U.S. Pat. No. 3,795,712 to Torck et al. relates to acid catalysts comprising a Lewis acid, a Bronsted acid, and a sulfone of the formula R-$SO_2$-R', where R and R' are each separately a monovalent radical containing from 1 to 8 carbon atoms or form together a divalent radical having from 3 to 12 carbon atoms. By dissolving the acid in a sulfone, the effective acid strength is said to be markedly increased.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,646,488 discloses an anhydrous nonalcoholic alkylation catalyst comprising a mixture of a mineral acid and an ether in proportion of from about 50 to about 99 weight percent of mineral acid and from about 1 to about 50 weight percent of ether. Useful mineral acids includes HF; see column 4 at lines 56-60.

Recently, research efforts have focused on Lewis acid promoted solids as alkylation catalysts. The term "Lewis acid" as used herein refers to a molecule which is capable of combining with another molecule or ion by forming a covalent chemical bond with two electrons from the second molecule or ion. Examples of Lewis acids include boron trifluoride ($BF_3$), boron trichloride ($BCl_3$), antimony pentafluoride ($SbF_5$), and aluminum chloride ($AlCl_3$). For a general discussion of Lewis acids, see *Friedel-Crafts and Related Reactions*, Interscience Publishers, Chapters III and IV (1963), which is incorporated herein by reference. The following U.S. Patents address alkylation in the presence of a Lewis acid-promoted solid and are incorporated by reference as if set forth at length herein.

U.S. Pat. No. 4,918,255 to Chou et al. teaches a process for alkylating an isoparaffin with an olefin in the presence of a catalyst complex comprising a Lewis acid and a large pore zeolite and/or a non-zeolitic inorganic solid, together with a controlled amount of water.

U.S. Pat. No. 4,935,577 to Huss, Jr. et al. discloses a catalytic distillation alkylation process employing a Lewis acid promoted solid catalyst comprising a non-zeolitic inorganic oxide, a large pore crystalline molecular sieve, and/or an ion exchange resin.

U.S. Pat. No. 4,992,616 to Chou et al. teaches catalytic isoparaffin:olefin alkylation in the presence of added water, a bound or unbound large pore zeolite, and a Lewis acid, wherein the Lewis acid is present in an amount exceeding that required to saturate the zeolite and its binder or matrix, if present.

The two-part article, "Modern Alkylation", by Lyle F. Albright, *Oil and Gas Journal*, Nov. 12 and 26, 1990, summarizes the state of the art in alkylation technology, and highlights problems associated with liquid Bronsted acid catalysts such as HF and $H_2SO_4$, and notes safety and environmental concerns associated with using and storing substantial quantities of these acids, which concerns underscore the desirability of developing a commercially viable low acid inventory isoparaffin:olefin alkylation process.

Various techniques have been explored for improving contact between a Bronsted acid catalyst and hydrocarbon reactants. For example, U.S. Pat. No. 3,780,130 describes a gas-fog alkylation process, wherein a fog or mist of acid is allowed to react with the hydrocarbon. Although this prior art noted some improvement in the alkylation process, very high voltages (up to 4000 v) are required for the generation of acid fog making the process impractical on a commercial scale.

In the process described in U.S. Pat. No. 2,380,234, a small amount of solid is dispersed in the acid phase. The resultant system shows limited improvement in the alkylation efficiency as shown by a slight increase in the alkylate yield.

More recently, U.S. Pat. No. 4,783,567, teaches a process wherein the hydrocarbon feed is contacted with hydrofluoric acid in a reactor with a fixed bed of a solid packing. The reference reported minor improvements associated with the use of solid packings.

Clearly then, it would be desirable to provide a catalyst system and alkylation process which not only produces high quality alkylate but also avoids the safety and environmental problems associated with Bronsted acid-catalyzed alkylation.

SUMMARY OF THE INVENTION

The present invention provides a process for alkylating an isoparaffin with an olefin comprising effecting reaction of isoparaffin and olefin in the presence of an alkylation catalyst complex comprising a Lewis acid and a solid component, said solid component comprising a layered silicate and pillars of an oxide of at least one element selected from Groups IB, IIB, IIIA, IIIB, IVA, IVB, VA, VB, VIA, VIIA and VIIIA of the Periodic Table of the Elements separately the layers of the silicate.

In a particularly preferred embodiment, the Lewis acid comprises $BF_3$, and the feedstock, comprising a mixture of butene and excess isobutane, reacts to evolve a high octane gasoline blending stock.

DETAILED DESCRIPTION

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

The weight ratio of isoparaffin to olefin in the total feed to the alkylation reaction zone is generally between 1.5:1 and 100:1, preferably between about 5:1 and about 50:1. Suitable total fresh feedstocks contain isoparaffin and olefin in isoparaffin:olefin weight ratio of from greater than about 1:1 up to about 10:1.

Process Conditions

The present alkylation process is suitably conducted at temperatures of from about −40° to about 500° C., preferably from about −40° to about 200° C., and more preferably below about 150° C. to avoid undesirable side reactions. Lower reaction temperatures are preferred to maximize alkylate octane. The upper temperature limit is more critical to avoid undesirable side reactions. Lower temperatures are generally preferred, for example temperatures as low as −20° C. may be effectively employed. Operating temperature typically falls within the range of about 0° to about 40° C.

Operating pressure is controlled to maintain the reactants in the liquid phase, and is suitably from about 50 to about 1500 psig, preferably from about 100 to about 500 psig. The catalyst weight hourly space velocity as well as the Lewis acid dosage varies with the particular combination of feedstream composition, Lewis acid, and pillared layered silicate employed.

Hydrocarbon and catalyst flow through the alkylation zone is typically controlled to provide weight hourly space velocity (WHSV) sufficient to convert about 99 percent by weight of fresh olefin to alkylate product. Typical WHSV values typically fall within the range of from about 0.01 to about 10 $hr^{-1}$.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

The particular reactor configuration selected for contacting the reactants and alkylation catalyst of the present invention is not critical, and both fixed-bed and stirred tank reactors may be used. As the reactants flow through the reactor, however, a portion of the Lewis acid is typically removed from the reactor with the effluent. For this reason, the Lewis acid contained in the reactor effluent stream is suitably separated (e.g., decanted) from the hydrocarbon portion of the stream and recycled. Additionally, fresh makeup Lewis acid is typically added as required to the reactor to maintain acid strength.

Water or water-forming materials may be added to the alkylation reaction zone, for example at a rate which averages from about 0.1 ppmw to about 1 wt. %, based on total hydrocarbon feed rate, preferably at a rate from about 0.1 to about 500 ppmw. The water can be supplied as such or be a feed material which provides water under the alkylation condition selected. Suitable water-forming materials include monohydric and dihydric alcohols which yield water upon undergoing dehydration. Of this group, particular preference is accorded the aliphatic alcohols, especially those containing 1 to 6 carbon atoms, for example, methanol, ethanol, isopropanol, t-butyl alcohol and isopentyl alcohol. The water and/or water-producing material can be added directly to the reactor, that is, as part of the feed and/or it can be incorporated in the catalyst, either by direct contact or by exposing the catalyst to an atmosphere of water and/or water-forming material. The amount of preintroduced water into the catalyst ranges from about 0.5 to about 25 percent by weight of the catalyst, preferably from about 1 to about 10 percent.

The Solid Component of the Alkylation Catalyst Complex

The solid component of the alkylation catalyst complex of the present invention comprises a pillared layered silicate as described herein. U.S. Pat. No. 5,008,481 to Johnson et al. teaches a pillared layered silicate containing a dehydrogenation metal which is useful for paraffin aromatization. The '481 Johnson et al. patent is incorporated by reference as if set forth at length herein for details of pillared layered silicate synthesis.

Many layered materials are known which have three-dimensional structures which exhibit their strongest chemical bonding in only two dimensions. In such materials, the stronger chemical bonds are formed in two-dimensional planes and a three-dimensional solid is formed by staking such planes on top of each other. However, the interactions between the planes are weaker than the chemical bonds holding an individual place together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the distance between the interlamellar layers can be increased substantially by absorption of various swelling agents such as water, ethylene glycol, amines, ketones, etc., which enter the interlamellar space and push the layers apart. However, the interlamellar spaced of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing." These values indicate the distance between, for example, the uppermost margin of one layer with the uppermost margin of its adjoining layer. If the layer thickness is known, the interlayer spacing can be determined by subtracting the layer thickness form the basal spacing.

The solid component of the alkylation catalyst complex employed in the present invention comprises a layered silicate containing interspathic polymeric oxide such as silica. The interlayer distance of the silicate may be such that polycyclic hydrocarbons can pass between adjacent layers of the silicate, preferably a distance greater than about 10 A or even 15 A, perhaps about 15 to 20 A.

The process of the present invention utilizes an alkylation catalyst complex which comprises a layered silicate containing interspathic polymeric silica. The layered silicate may also comprise an interspathic polymeric oxide of an element selected from the group consisting of Al, B, Cr, Ga, In, Mo, Nb, Ni, Ti, Tl, W, and Zr, e.g., polymeric silica-alumina between the layers of the silicate material. Preferably, such "pillared" materials are thermally stable, i.e., capable of withstanding calcining at a temperature of about 450° C. for at least 2 hours without significant reduction, e.g., not greater than 10 or 20 percent, in the spacing between the silicate layers. Preferably, such materials can withstand prolonged exposure to the conditions encountered during alkylation. Polymeric interspathic silicas displaced between silicate layers are considered to include oxides of two or more reporting units, e.g., four or more or even five or more repeating units. The extent of polymerization of the interspathic polymeric silica is believed to effect the ultimate interlayer separation of the layered product; that is to say, the greater the extent of polymerization occuring, the greater the interlayer distance resulting in the pillared layered silicate. A layered material suited for use in the present alkylation process, having a desired interlayer spacing can be prepared according to the method set out in U.S. Pat. No. 4,859,648 to Landis et al., incorporated herein by reference. In this method, the interlayer spacing of the layered material can be tailored by careful selection of the "propping" agent used to separate the layers during treatment with interspathic polymeric silica precursors which are eventually converted to the thermally stable polymeric silica "pillars." Indeed, a wide range of interlayer spacings can be achieved by this method. Interlayer distances can range anywhere from 2 to 30 A or more, e.g., greater than 5, 10, 15, or 20 A, depending largely on the type of "propping" agent used as well as the layered silicate being treated.

The pillared layered silicates employed herein can be prepared by treating a layered silicate which contains ion exchange sites having interspathic cations associated therewith, with an organic compound which is a cationic species or capable of forming a cationic species to effect exchange with the interspathic cations. An electrically neutral compound capable of conversion to the interspathic polymeric metal or non-metal oxide is provided between the layers of the treated layered silicate. The compound is then converted to the interspathic polymeric silica to form the layered material.

The pillared layered silicate employed in the present invention can be prepared by treating a layered silicate, e.g., a high silica alkali silicate such as synthetic magadiite, or synthetic kenyaite. These pillared layered silicate materials possess a framework composed essentially of only tetrahedral sheets, i.e., silicon is coordinated with four oxygen atoms, condensed on each other. These materials lack octahedral sheets, such as those found in clays, wherein an element such as aluminum is coordinated with six oxygen atoms. Besides the interspathic polymeric silica, interspathic polymeric oxides of one or more elements selected from the group consisting of B, Al, Ga, In, and Tl can also be incorporated between the layers of the silicate either separate from or incorporated into the interspathic polymeric silica pillars. Interspathic polymeric alumina is particularly useful in imparting acidic activity to the layered silicate. Interspathic polymeric oxides containing silica-alumina are a preferred pillar for these layered silicates.

Pillared silicates containing from about 5 to 50 wt % silica-alumina incorporated as the pillar material are desirable. Particularly preferred are silicates containing from about 10 to 20 wt % silica-alumina as the pillared material. The silica/alumina molar ratio ($SiO_2/Al_2O_3$) of the pillared material may vary between about 5 to 1000 or even greater.

Layered silicate materials of relatively high interplanar distance (d-spacing), e.g., greater than about 10, 15, 18, 20, 25, or even 30 or more A, can be prepared using the above-discussed techniques. These materials are capable of being exposed to severe conditions such as those encountered in calcining, e.g., at temperatures of about 450° C. for about two or more hours, e.g., four hours, in nitrogen or air, without significant decrease, perhaps, e.g., less than about 10 percent, in interlayer distance. Charge density should be taken into consideration in determining the suitability of the cationic species introduced between the layers in the procedure used to prop open the layers prior to pillaring. The use of an electrically neutral polymeric oxide precursor allows the formation of materials in which the interlayer spacing can be widely varied.

The layered silicate starting material can contain ion exchange sites having interspathic cations associated therewith. Such interspathic cations may include hydrogen ion, hydronium ion or alkali metal cation. The starting material is treated with a "propping" agent comprising a source of organic cation, which source may include the cation itself, in order to effect an exchange of the interspathic cations resulting in the layers of the starting material being propped apart. In particular, alkylammonium cations have been found useful. The $C_3$ and large alkylammonium cations, e.g., n-octylammonium, can be readily incorporated within the interlayer species of the layered silicates, serving to prop open the layers in such a way as to allow incorporation of the polymeric oxide precursor. The extent of the interlayer spacing can be controlled by the size of the organoammonium ion employed so that use of the n-propylammonium cation can achieve a d-spacing of about 2 to 5 A or an opening of about 2–3 A, whereas to achieve an interlayer opening of 10 to 20 A, an n-octylammonium cation or a cation of equivalent length is required. The organic ammonium cations separating the silicate layers may also be formed in situ by reaction of the neutral amine species with interlayer hydrogen or hydronium cations of the layered silicate starting material.

The polymeric oxide pillars are formed from a precursor material which is preferably introduced between the layers of the organic "propped" species as a cationic, or more preferably, electrically neutral, hydrolyzable compound of the desired elements. The precursor material is preferably an organic compound containing said desired elements which is a liquid under ambient conditions. In particular, hydrolyzable compounds, e.g., alkoxides, of the desired elements of the pillars are utilized as the precursors. Suitable polymeric silica precursor materials include tetraalkylsilicates, e.g., tetrapropylorthosilicate, tetramethylorthosilicate, and, most preferably, tetraethylorthosilicate. Introduction of interspathic polymeric oxide of an element selected from the group consisting of Al, B, Cr, Ga, In, Mo, Nb, Ni, Ti, Tl, W, and Zr to the pillar system can be achieved by contacting a hydrolyzable compound of the desired element with the organic "propped" species before, after or simultaneously with the contacting of the layered chalcogenide with the silicon compound. The hydrolyzable aluminum compound employed may be an aluminum alkoxide, e.g., aluminum isopropoxide.

After hydrolysis to produce the polymeric oxide pillars and calcination to remove the organic propping agent, the final pillared product may contain residual exchangeable cations. Such residual cations in the layered material can be ion exchanged by known methods with other cationic species to provide or alter the catalytic activity of the pillared product. Base metal or noble components containing at least one element selected from the group consisting of Cr, Mo, W, Fe, Co, Ni, Ru, Rh, Pd, Os, Ir, and Pt, can be introduced by ion-exchange or impregnation techniques known in the art. Representative ion exchange techniques are disclosed in a wide variety of patents including U.S. Pat. Nos. 3,140,249; 3,140,251; and 3,140,253, all of which are incorporated herein by reference. While various metals may optionally be introduced by the techniques described above, it is to be understood that such addition is not required and that the alkylation process of the present invention proceeds in the absence of such added metals.

The polymeric oxide precursor-containing product can be exposed to suitable conversion conditions, such as hydrolysis and/or calcination to form the layered material employed in the present invention. The hydrolysis step may be carried out by any method, for example, by interspathic water already present in the organic-"propped" layered silicate material. Because of the effect of interspathic water on hydrolysis, the extent of hydrolysis may be modified by varying the extent to which the organic-"propped" species is dried prior to addition of the polymeric oxide precursor. As noted earlier, the product after conversion to the polymeric oxide form may be exposed to conditions which remove organic compounds such as the organic cation propping agents, e.g., exposure to elevated temperatures such as those encountered by calcining in air or nitrogen. Such products, especially when calcined, exhibit high surface area, e.g., greater than 200, 300, 400 or even 600 $m^2/g$, and thermal and hydrothermal stability.

The pillared silicates can be composited with porous inorganic oxide matrix materials such as silica-alumina, silica-magnesia, silica-zirconia, silica-thoria, silica-beryllia, and silica-titania, as well as ternary compositions, such as silica-alumina-thoria, silica-alumin-zirconia, silica-alumina-magnesia, and silica-magnesia-zirconia. The matrix may be in the form of a cogel. The relative proportions of pillared silicate component and inorganic matrix, on an anhydrous basis, may vary widely with the silicate content ranging from about 1 to about 99 wt % and more usually in the range of from about 5 to about 80 wt % of the dry composite.

Layered silicates, e.g., high silica alkali silicates such as magadiite, natrosilite, kenyaite, makatite, nekoite, kanemite, okenite, dehayelite, macdonaldite and rhodesite, unlike swellable clays, lack octahedral sheets, i.e., sheets composed of atoms which are octahedrally coordinated with oxygen atoms. Such high silica alkali silicates, as well as their synthetic analogues, are well-suited as starting materials used in preparing the pillared layered silicates employed in the process of the present invention. Without stable intercalated pillars, these starting materials tend to undergo collapse of their layers at elevated temperatures, which results in low porosity and low surface area.

The layered silicate starting materials known as high silica alkali silicates, whose layers lack octahedral sheets, can be prepared hydrothermally from an aqueous reaction mixture containing silica and caustic at relatively moderate temperatures and pressures. These layered silicates may contain tetracoordinate framework atoms other than Si. Such layered silicates can be prepared by co-crystallizing in the presence of non-silicon tetravalent elements, e.g., those selected from the group consisting of B, Al, Ga, In, and Tl as well as any other such elements which are catalytically useful when incorporated in the silicate structure. Alternatively, non-silicon framework elements already in a layered silicate may be substituted by a tetracoordinate element. Both co-crystallized and substituted layered high silica alkali silicates may be treated by the procedure described above to provide layered materials containing interspathic polymeric oxide pillars.

Synthetic magadiite materials which contain interspathic polymeric oxides may be particularly suited to use in the alkylation process of the present invention. Synthetic magadiite is readily synthesized hydrothermally from a reaction mixture containing expensive sources of silica and caustic. Tetracoordinate elements other than silicon, e.g., those selected from the group consisting of B, Al, Ga, In, Tl and other catalytically useful metals, may be added to the reaction mixture to produce synthetic magadiite layered silicates. Preferably, such elements are selected from the group consisting of Al and Ga. An organic directing agent may also be added to the reaction mixture. The reaction mixture for synthetic layered silicate materials can be described in molar ratios as follows:

$SiO_2/X_2O_3 = 10$ to infinity where X can be B, Al, B, Ga, In, and/or Tl or other catalytically useful metal $M^+OH^-/SiO_2 = 0$ to 0.6 (preferably 0.1–0.6) M = an alkali metal $H_2O/SiO_2 = 8-500$ $R/SiO_2 = 0-0.4$ where R can be an organic such as benzyltriethylammonium chloride, benzyltrimethylammonium chloride, dibenzyldimethylammonium chloride, N, N-dimethylpiperazine, triethylamine, or other quaternary compounds or heterocyclic amines.

The reaction mixture can be maintained at a temperature of about 100° to 200° C. for anywhere from about 1 to 150 days in order to form a product having the following composition:

% N=0 to 3, e.g., 0 to 0.3

$SiO_2/X_2O_3 = 10$ to infinity where X may be in the tetrahedral or octahedral position $M_2O/SiO_2 = 0$ to 0.5, e.g., 0.05–0.1

The synthetic layered silicate materials thus prepared have a low surface area. Introduction of interspathic polymeric oxides according to the above-described procedure can increase the surface area of these materials. Generally, the synthetic magadiite (or layered silicate) material is acidified by any suitable means, e.g., treatment with aqueous 0.1N HCl, and thereafter treated with a "propping" agent. A suitable compound capable of conversion to a polymeric oxide is combined with the "propped" layered silicate and the resulting material can then be calcined to remove residual organics.

Another embodiment of the present invention involves alkylation reactions using synthetic kenyaite materials which contain interspathic polymeric oxides. Kenyaite, a layered silicic acid which is known to exist in nature as a sodium salt ($Na_2Si_{22}O_{45}H_2O$), can be prepared in the potassium form $K_2Si_{22}O_{45}10H_2O$ in the laboratory. Synthetic kenyaite is readily synthesized hydrothermally from a reaction mixture containing inexpensive sources of silica and caustic, preferably KOH. Tetracoordinate elements other than silicon, e.g., those selected from the group consisting of Al, B, Cr, Fe, Ga, In, Ni, Zr and other catalytically useful metals, may be added to the reaction mixture to produce synthetic kenyaite layered silicates. $Al(NO_3)_3 \cdot 9H_2O$ and aluminum-tri-sec-butoxide are suitable reagents for introduction of non-silicon tetracoordinate elements in the kenyaite framework. Co-crystallizing with B, Al, and/or Zr is particularly preferred. The reaction mixture may also be seeded with kenyaite.

EXAMPLES

Synthetic kenyaite as produced in Example 25 of U.S. Pat. No. 4,859,648 (1000 gm) was added to cetyldimethylethylammonium bromide (2000 mls), stirred at room temperature for about 16 hours, filtered, washed with water, and air dried. This exchange procedure was repeated for a total of two exchanges. The air-dried product (300 gm) was then impregnated with tetraethylorthosilicate (300 gm) and the vessel, a closed polypropylene jar, was rolled on a roller for about 16 hrs to ensure thorough mixing. The product was filtered and allowed to air-dry. The product was slurried in water (500 g) for 2 hrs, again filtered and air-dried to a powder. The product was calcined at 540° C. for 6 hours. Product properties are given below in Table 1.

TABLE 1

| Pillared Layered Silicate Product Properties | |
|---|---|
| Surface Area, $M^2/g$ | 554 |
| Adsorption, wt % | |
| n-hexane | 16.3 |
| cyclohexane | 18.7 |
| water | 9.7 |

EXAMPLES 2 AND 3

In the start-up procedure for Examples 2 and 3, 10 grams of catalyst were placed in a 300 cc reactor, and about 300 cc of isobutane were charged to fill the reactor. When the resulting mixture was cooled to the desired temperature with constant stirring at about 2000 rpm, $BF_3$ gas was introduced to the reactor. After $BF_3$ breakthrough was observed, the $BF_3$ flow rate was then reduced to a level equivalent to 3 wt % of total hydrocarbons processed. At this point, the 15/1 isobutane/2-butene feed was continuously fed into the reactor to initiate alkylation. The operating conditions throughout the run were 150 psig, 32°/68° F., 2000 rpm, 0.9–1.2 hr$^{-1}$ WHSV based on olefin and 3 wt % $BF_3$ based on total hydrocarbon feed. Reactor effluent was continuously withdrawn through a back pressure regulator and then sent to a receiver which was maintained at 0° C. and atmospheric pressure. Periodically, the product was drained from the receiver and weathered at room temperature prior to analysis.

A liquid on-line gas chromatograph coupled with an automatic sampling device was employed to monitor the course of the alkylation reaction. All of the samples (on-line, gas and liquid) were analyzed by a fused silica capillary column (Alltech's Durabond DB-1). All reported octane numbers are measured values.

The data contained in Table 2 demonstrates that the $BF_3$-promoted pillared layered silicate alkylation catalyst complex of the invention produces high quality alkylate when processing 15/1 isobutane/2-butene feed. The alkylates produced at 32° and 68° F. with the 15/1 isobutane/2-butene feed had octanes of 97 and 95 R+M/2, respectively, which is comparable to that produced commercially with HF and sulfuric acid catalysts.

TABLE 2

BF$_3$/MCM-25(Si) Catalyzed Alkylation
of Isobutane/2-Butene Feed
Catalyst: BF$_3$-promoted Pillared Layered Silicate of
Example 1

|  | Example 2 | Example 3 |
|---|---|---|
| Reaction Conditions |  |  |
| Reactor Temperature (°F.) | 68 | 32 |
| Reactor Pressure (psig) | 150 | 150 |
| Olefin WHSV (hr$^{-1}$) | 0.9 | 0.9 |
| BF$_3$ Cofeed Rate (wt %) | 3.0 | 3.0 |
| Feed Composition, wt % |  |  |
| 2-Butene | 5.8 | 5.8 |
| Isobutane | 94.0 | 94.0 |
| n-paraffins | 0.2 | 0.2 |
| Time On-Stream, hrs | 10 | 49 |
| Olefin Conversion, wt % | 100 | 100 |
| Product Composition, wt % |  |  |
| C$_5$-C$_7$ | 10.8 | 4.1 |
| C$_8$'s | 86.0 | 93.0 |
| C$_9$$^+$ | 3.2 | 2.9 |
| TMP/DMH* | 4.1 | 7.4 |
| Raw Gasoline Octanes |  |  |
| R + O | 95.5 | 99.0 |
| M + O | 94.4 | 95.8 |
| R + M/2 | 95.0 | 97.4 |

*Ratio of high octane trimethylpentanes (TMP) to lower octane dimethylhexanes (DMH).

Changes and modifications in the specifically described embodiments can be carried out without departing from the scope of the invention which is intended to be limited only by the scope of the appended claims.

What is claimed is:

1. A process for alkylating an isoparaffin with an olefin comprising effecting reaction of isoparaffin and olefin in the presence of an alkylation catalyst complex comprising a Lewis acid-promoted solid component said solid component comprising a layered silicate and pillars of an oxide of at least one element selected from Groups IB, IIB, IIIA, IIIB, IVA, IVB, VA, VB, VIA, VIIA and VIIIA of the Periodic Table of the Elements separating the layers of the silicate.

2. The process of claim 1 wherein the isoparaffin contains from 4 to 6 carbon atoms and the olefins contains from 2 to 6 carbon atoms.

3. The process of claim 1 wherein the Lewis acid is selected from the group consisting of BF$_3$, SbF$_5$ and AlCl$_3$.

4. The process of claim 1 wherein the pillars comprise polymeric silica.

5. The process of claim 1 wherein said layered silicate is selected from the group consisting of magadiite, natrosilite, kenyaite, makatite, nekoite, kenemite, okenite, dehayelite, macdonaldite, and rhodesite.

6. The process of claim 5 wherein said layered silicated is kenyaite.

7. The process of claim 1 wherein the molar ratio of the isoparaffin to the olefin is from about 5:1 to about 50:1.

8. The process of claim 1 wherein the isoparaffin is isobutane and the olefin feed is a mixture of propylene and butenes.

9. The process of claim 1 wherein water and/or water-producing material is preintroduced into the catalyst complex.

10. The process of claim 9 wherein the amount of water preintroduced into the catalyst complex ranges from about 0.25 to about 25 percent by weight of the catalyst complex.

11. The process of claim 9 wherein the amount of water preintroduced into the catalyst complex ranges from about 1.0 to about 10 percent by weight of the catalyst complex.

12. The process of claim 1 wherein water and/or water-producing material is cofed with the reactants.

13. The process of claim 11 wherein the amount of water ranges from about 0.1 ppmw to about 1 weight percent based upon the total hydrocarbon feed rate.

* * * * *